US012782308B2

(12) United States Patent
Ciou et al.

(10) Patent No.: US 12,782,308 B2
(45) Date of Patent: Nov. 3, 2026

(54) METHOD OF MANUFACTURING A NON-POLAR VOLATILE ORGANIC CHEMICAL SENSOR

(71) Applicant: Nanyang Technological University, Singapore (SG)

(72) Inventors: Jing Hao Ciou, Singapore (SG); Pooi See Lee, Singapore (SG)

(73) Assignee: Nanyang Technological University, Singapore (SG)

( * ) Notice: Subject to any disclaimer, the term of this patent is extended or adjusted under 35 U.S.C. 154(b) by 515 days.

(21) Appl. No.: 18/556,802

(22) PCT Filed: May 17, 2022

(86) PCT No.: PCT/SG2022/050324
§ 371 (c)(1),
(2) Date: Oct. 23, 2023

(87) PCT Pub. No.: WO2022/245289
PCT Pub. Date: Nov. 24, 2022

(65) Prior Publication Data

US 2024/0219334 A1 Jul. 4, 2024

(30) Foreign Application Priority Data

May 17, 2021 (SG) ............................ 10202105123P

(51) Int. Cl.
*G01N 27/12* (2006.01)
*G01N 33/00* (2006.01)

(52) U.S. Cl.
CPC ......... *G01N 27/12* (2013.01); *G01N 33/0027* (2013.01)

(58) Field of Classification Search
None
See application file for complete search history.

(56) References Cited

U.S. PATENT DOCUMENTS

2019/0391099 A1 12/2019 Jung et al.
2020/0029858 A1 * 1/2020 Reddy .................... G16H 40/67

FOREIGN PATENT DOCUMENTS

WO 2020242387 A1 12/2020

OTHER PUBLICATIONS

Chen, W.Y., et al., Surface Functionalization of Ti3C2Tx MXene with Highly Reliable Superhydrophobic Protection for Volatile Organic Compounds Sensing. ACS nano, 2020.

(Continued)

*Primary Examiner* — Kathryn Elizabeth Limbaugh
(74) *Attorney, Agent, or Firm* — Patterson + Sheridan, LLP

(57) ABSTRACT

Disclosed herein is a method of manufacturing a non-polar volatile organic chemical sensor, the method requiring the steps of providing a composite material comprising a substrate coated by an activated Ti3C2 MXene layer, which activated Ti3C2 MXene layer has a surface and forming a hydrophobic silane layer on the surface of the activated Ti3C2 MXene layer to provide the non-polar volatile organic chemical sensor, where the hydrophobic silane layer is formed by gaseous phase silanization using a monomeric hydrophobic silane compound. Also disclosed herein is a non-polar volatile organic chemical sensor and its use to detect non-polar volatile organic compounds.

19 Claims, 4 Drawing Sheets

(56) References Cited

OTHER PUBLICATIONS

Farmer, E.E. and C.A. Ryan, Interplant communication: airborne methyl jasmonate induces synthesis of proteinase inhibitors in plant leaves. Proceedings of the National Academy of Sciences, 1990. 87(19): p. 7713-7716.
Halim, J., et al., X-ray photoelectron spectroscopy of select multi-layered transition metal carbides (MXenes). Applied Surface Science, 2016. 362: p. 406-417.
Howe, G.A. and G. Jander, Plant immunity to insect herbivores. Annu. Rev. Plant Biol., 2008. 59: p. 41-66.
Kessler, A. and I.T. Baldwin, Defensive function of herbivore-induced plant volatile emissions in nature. Science, 2001. 291(5511): p. 2141-2144.
Lackus, N.D., et al., The occurrence and formation of monoterpenes in herbivore-damaged poplar roots. Scientific reports, 2018. 8(1): p. 1-13.
Lee, E., et al., Room temperature gas sensing of two-dimensional titanium carbide (MXene). ACS applied materials & interfaces, 2017. 9(42): p. 37184-37190.
Shah, S., et al., Template-free 3D titanium carbide (Ti 3 C 2 T x) MXene particles crumpled by capillary forces. Chemical Communications, 2017. 53(2): p. 400-403.
Shuvo, S.N., et al., Sulfur-Doped Titanium Carbide MXenes for Room-Temperature Gas Sensing. ACS sensors, 2020. 5(9): p. 2915-2924.
Wu, M., et al., Ti3C2 MXene-based sensors with high selectivity for NH3 detection at room temperature. ACS sensors, 2019. 4(10): p. 2763-2770.
Xiao, B., et al., MXenes: Reusable materials for NH3 sensor or capturer by controlling the charge injection. Sensors and Actuators B: Chemical, 2016. 235: p. 103-109.
International Search Report and Written Opinion in related application PCT/SG2022/050324 dated Sep. 28, 2022.
Steinbach, A.M. et al., Gas phase silanization for silicon nanowire sensors and other lab-on-a-chip systems. physica status solidi c, Nov. 19, 2015, vol. 13, No. 4, pp. 135-141 [Retrieved on Aug. 29, 2022] <DOI: 10.1002/PSSC.201510211 > the whole document.
Munief, WM. et al., Silane Deposition via Gas-Phase Evaporation and High-Resolution Surface Characterization of the Ultrathin Siloxane Coatings. Langmuir, Aug. 7, 2018, vol. 34, No. 35, p. 10217-10229 [Retrieved on Aug. 29, 2022] <DOI: 10.1021/ACS.LANGMUIR.8B01044> the whole document.
Chen, WY. et al., Surface Functionalization of Ti3C2Tx MXene with Highly Reliable Superhydrophobic Protection for Volatile Organic Compounds Sensing. ACS Nano, Aug. 28, 2020, vol. 14, No. 9, pp. 11490-11501 [Retrieved on Aug. 29, 2022] <DOI: 10.1021 /ACSNANO.0C03896> the whole document.

* cited by examiner

METHOD OF MANUFACTURING A NON-POLAR VOLATILE ORGANIC CHEMICAL SENSOR

FIELD OF INVENTION

The current invention relates to a method of making $Ti_3C_2$ MXenes that are useful in the detection of volatile organic compounds from plants. The invention also relates to their use in sensors.

BACKGROUND

The listing or discussion of a prior-published document in this specification should not necessarily be taken as an acknowledgement that the document is part of the state of the art or is common general knowledge.

Due to the hydrophilic nature of pristine $Ti_3C_2$ MXene, high sensing response towards polar volatile organic compounds (VOCs) or gas, especially $NH_3$ gas (E. Lee et al., *ACS Appl. Mater. Interfaces* 2017, 9, 37184-37190; M. Wu et al., *ACS Sens.* 2019, 4, 2763-2770; and B. Xiao et al., *Sens. Actuators B Chem.* 2016, 235, 103-109), has been reported. However, there is still a lack of reports investigating $Ti_3C_2$ MXene for the sensing of non-polar VOCs. The only one work related to non-polar VOC sensing by $Ti_3C_2$ MXene was reported by Shuvo et al. (S. N. Shuvo et al., *ACS Sens.* 2020, 5, 2915-2924). The sulfur-doped $Ti_3C_2$ MXene presents the highest sensing response for analytes such as hexyl acetate, hexane and ethanol.

Apart from the common non-polar VOCs like toluene, there is another large group of hydrocarbons called terpenes. Terpenes contain diverse types of non-polar molecules. Interestingly, terpenes often have a certain odour, which deters an herbivore or attracts the predator of herbivores. In addition, the release of this kind of "signal" VOCs was also found to induce interplant communication for the defensive response to herbivores. Thus, the ability to detect these inter-plant communication signals would be a promising technique in farmland management and help to alarm the possible spread of plant disease or pest.

Therefore, there exists a need to discover new derivatives of $Ti_3C_2$ MXenes for the detection of plant VOCs.

SUMMARY OF INVENTION

Aspects and embodiments of the current invention will now be discussed by reference to the following numbered clauses.

1. A method of manufacturing a non-polar volatile organic chemical sensor, the method comprising the steps of:
(a) providing a composite material comprising a substrate coated by an activated $Ti_3C_2$ MXene layer, which activated $Ti_3C_2$ MXene layer has a surface; and
(b) forming a hydrophobic silane layer on the surface of the activated $Ti_3C_2$ MXene layer to provide the non-polar volatile organic chemical sensor, wherein the hydrophobic silane layer is formed by gaseous phase silanization using a monomeric hydrophobic silane compound.
2. The method according to Clause 1, wherein the monomeric hydrophobic silane compound is selected from one or more of the group consisting of (3-aminopropyl) trimethoxysilane (APTMS), trimethoxy(octyl)silane (TEOS), trimethoxy(propyl)silane, and trimethoxymethylsilane (TEMS).

3. The method according to Clause 2, wherein the monomeric hydrophobic silane compound is trimethoxy(propyl)silane.
4. The method according to any one of the preceding clauses, wherein the hydrophobic silane layer has a thickness of from 10 to 14 nm.
5. The method according to any one of the preceding clauses, wherein the gaseous phase silanization is conducted at from 80 to 150° C., such as about 100° C. and a pressure of from 0.1 to 0.3 mbar, such as about 0.16 mbar.
6. The method according to any one of the preceding clauses, wherein the gaseous phase silanization used a flow of an inert gas at a flow rate of from 50 to 100 sccm, such as about 65 sccm, optionally wherein the inert gas is argon.
7. The method according to any one of the preceding clauses, wherein the composite material provided in step (a) of Clause 1 further comprises at least two electrodes laid on the surface of the activated $Ti_3C_2$ MXene layer.
8. The method according to Clause 7, wherein the electrodes are formed by thermal evaporation of an electrode material onto the surface of the activated $Ti_3C_2$ MXene layer, optionally wherein:
(i) the electrode material is gold; and/or
(ii) the at least two electrodes each have a thickness of from 75 to 150 nm, such as about 100 nm.
9. The method according to any one of the preceding clauses, wherein the activated $Ti_3C_2$ MXene layer is formed by the steps of:
(ai) providing a composite material comprising a substrate coated by an unactivated $Ti_3C_2$ MXene layer; and
(aii) activating the $Ti_3C_2$ MXene layer through a surface activation process.
10. The method according to Clause 9, wherein the surface activation process is plasma activation, optionally wherein the plasma activation is $O_2$ plasma activation.
11. A non-polar volatile organic chemical sensor comprising:
a substrate having a substrate surface;
a $Ti_3C_2$ MXene layer coated on the substrate surface which $Ti_3C_2$ MXene layer has a $Ti_3C_2$ MXene layer surface;
at least two electrodes on the $Ti_3C_2$ MXene layer surface; and
a hydrophobic silane layer on the $Ti_3C_2$ MXene layer surface, wherein the hydrophobic silane layer has a thickness of from 10 to 14 nm.
12. The sensor according to Clause 11, wherein the hydrophobic silane layer is formed from a monomeric hydrophobic silane compound that is selected from one or more of the group consisting of (3-aminopropyl) trimethoxysilane (APTMS), trimethoxy(octyl)silane (TEOS), trimethoxy(propyl)silane, and trimethoxymethylsilane (TEMS).
13. The sensor according to Clause 12, wherein the monomeric hydrophobic silane compound is trimethoxy(propyl)silane (TMPS).
14. The sensor according to any one of Clauses 11 to 13, wherein:
(I) the electrode material is gold; and/or
(II) the at least two electrodes each have a thickness of from 75 to 150 nm, such as about 100 nm.
15. The sensor according to any one of Clauses 11 to 14, wherein the non-polar volatile organic chemical sensor is capable of detecting an analyte present in an environment in a concentration of about 50 ppm.

16. A method of detecting an analyte comprising the steps of:

(bi) exposing a non-polar volatile organic chemical sensor as described in any one of Clauses 11 to 14 to an environment where the analyte is suspected to be present for a period of time; and (bii) subsequently measuring the resistance of the volatile organic chemical sensor to determine the presence or absence of the analyte in said environment.

17. The method according to Clause 16, wherein the analyte is a volatile organic compound.

18. The method according to Clause 17, wherein the volatile organic compound is selected from one or more of α-pinene, 1-hexanol, a terpinol, and phenethyl alcohol, optionally wherein the volatile organic compound is α-pinene.

19. The method according to any one of Clauses 16 to 18 wherein the non-polar volatile organic chemical sensor is capable of detecting an analyte present in the environment in a concentration of about 50 ppm.

DRAWINGS

Figure 5:
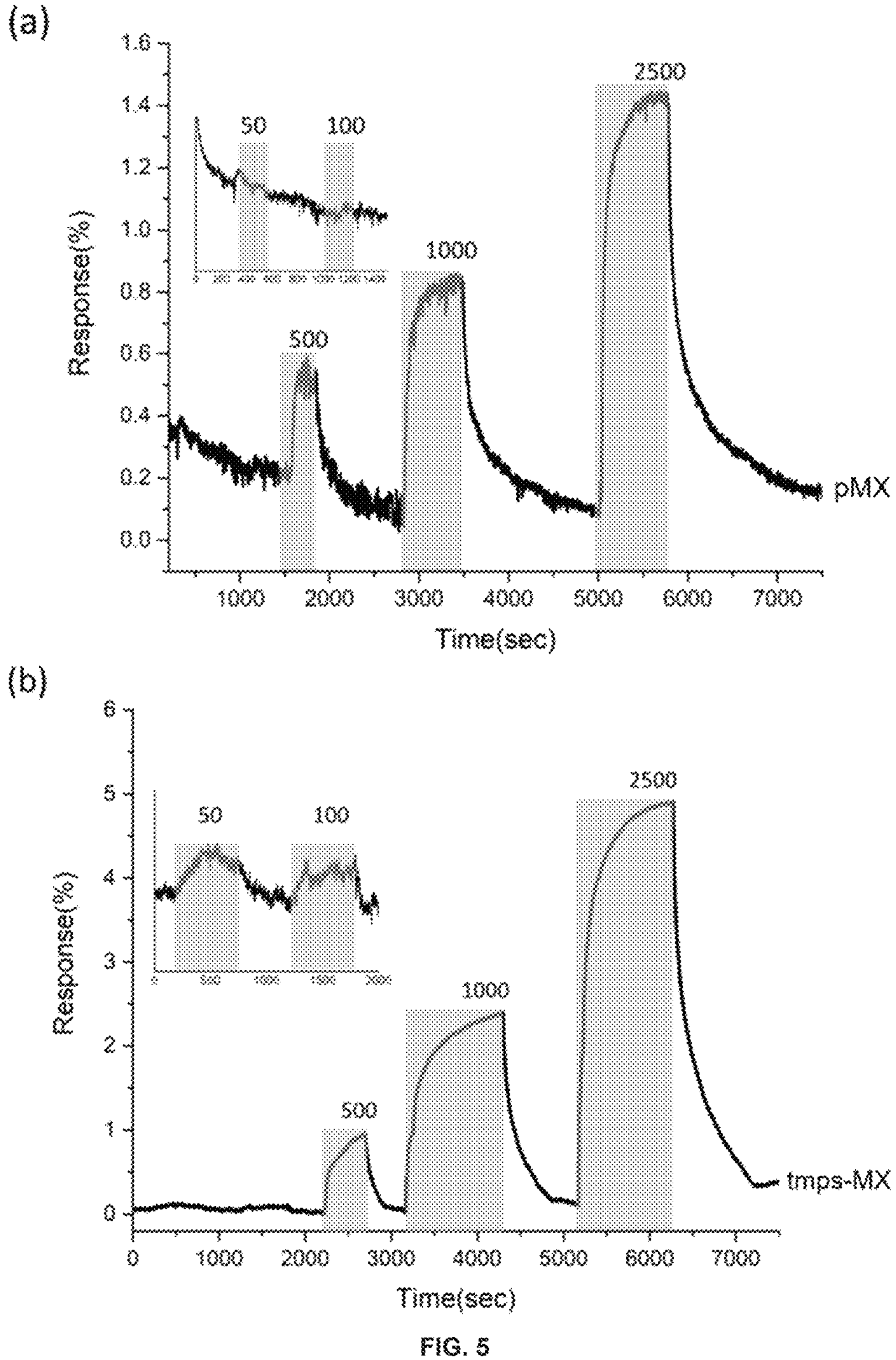

FIG. 5 depicts (a) the dynamic gas sensing response of pristine $Ti_3C_2$ MXene (pMX) VOC sensor with the zoom in view inset from 0 s to 1400 s. The orange blocks highlight the time period with the α-Pinene purging in the testing chamber with the purging time: 50 ppm: 300 sec, 100 ppm: 300 sec, 500 ppm: 300 sec, 1000 ppm: 650 sec; and 2500 ppm: 800 sec; and (b) the dynamic gas sensing response of TMPS-modified $Ti_3C_2$ MXene (tmps-MX) VOC sensor with zoom in view inset from 0 s to 2000 s. The orange blocks highlight the time period with the α-Pinene purging in the testing chamber with the purging time: 50 ppm: 400 sec, 100 ppm: 600 sec, 500 ppm: 600 sec, 1000 ppm: 1150 sec; and 2500 ppm: 1100 sec.

DESCRIPTION

It has been surprisingly found that a sensor with superior properties can be manufactured. Thus, in a first aspect of the invention there is provided a method of manufacturing a non-polar volatile organic chemical sensor, the method comprising the steps of:

(a) providing a composite material comprising a substrate coated by an activated $Ti_3C_2$ MXene layer, which activated $Ti_3C_2$ MXene layer has a surface; and (b) forming a hydrophobic silane layer on the surface of the activated $Ti_3C_2$ MXene layer to provide the non-polar volatile organic chemical sensor, wherein the hydrophobic silane layer is formed by gaseous phase silanization using a monomeric hydrophobic silane compound.

This sensor has been shown to be particularly useful in the detection of VOCs derived from plants. For example, the sensors manufactured by the process outlined above may be able to detect non-polar VOC analytes down to 50 ppm.

In embodiments herein, the word "comprising" may be interpreted as requiring the features mentioned, but not limiting the presence of other features. Alternatively, the word "comprising" may also relate to the situation where only the components/features listed are intended to be present (e.g. the word "comprising" may be replaced by the phrases "consists of" or "consists essentially of"). It is explicitly contemplated that both the broader and narrower interpretations can be applied to all aspects and embodiments of the present invention. In other words, the word "comprising" and synonyms thereof may be replaced by the phrase "consisting of" or the phrase "consists essentially of" or synonyms thereof and vice versa.

The phrase, "consists essentially of" and its pseudonyms may be interpreted herein to refer to a material where minor impurities may be present. For example, the material may be greater than or equal to 90% pure, such as greater than 95% pure, such as greater than 97% pure, such as greater than 99% pure, such as greater than 99.9% pure, such as greater than 99.99% pure, such as greater than 99.999% pure, such as 100% pure.

As will be appreciated, MXenes are 2-dimensional materials, one of which is $Ti_3C_2$. When used herein, a "$Ti_3C_2$ MXene layer" refers to a layer on a substrate that comprises (or consists of) $Ti_3C_2$ MXene compounds.

When used herein, the term "activated $Ti_3C_2$ MXene layer" refers to the surface of the $Ti_3C_2$ MXene layer where the surface has been chemically activated in any suitable way. Such surface activations may include plasma activation (e.g. with any suitable plasma, such as oxygen plasma, and the like).

When used herein, the term "hydrophobic" refers to a material that, when provided as an outer layer (i.e. as a surface), has a water contact angle of greater than 90°.

Sensors made using $Ti_3C_2$ MXene have not been particularly good at sensing non-polar VOCs, such as toluene and plant VOCs (e.g. terpenes). In the current invention the hydrophilic $Ti_3C_2$ MXene surface is coated with a hydrophobic silane (e.g. an alkyl silane, such as trimethoxy (propyl)silane (TMPS)) which replaces (or caps) the hydroxyl groups of $Ti_3C_2$ MXene by a hydrophobic group (e.g. a carbon chain). Without wishing to be bound by theory, it is believed that the existence of the hydrophobic groups (e.g. carbon chain) can improve the affinity of the non-polar VOCs towards the $Ti_3C_2$ MXene, thereby increasing the sensing response of the non-polar VOCs.

As noted above, the hydrophobic silane layer on the surface of the activated $Ti_3C_2$ MXene layer may be formed using a monomeric hydrophobic silane compound. Any suitable monomeric hydrophobic silane compound (or combination thereof) may be used herein. For example, the monomeric hydrophobic silane compound may include, but is not limited to, (3-aminopropyl)trimethoxysilane (APTMS), trimethoxy(octyl)silane (TEOS), trimethoxy (propyl)silane, trimethoxymethylsilane (TEMS), and combinations thereof. In particular embodiments that may be mentioned herein, the monomeric hydrophobic silane compound may be trimethoxy(propyl)silane (TMPS).

The hydrophobic silane layer on the surface of the activated $Ti_3C_2$ MXene layer may have any suitable level of thickness, provided that it still allows some form of interaction between the material to be sensed and the $Ti_3C_2$ MXene layer. For example, the hydrophobic silane layer may have a thickness of from 10 to 14 nm.

In order for the monomeric hydrophobic silane compound to form the hydrophobic silane layer on the surface of the activated $Ti_3C_2$ MXene layer, it needs to undergo a gaseous phase silanization process. This process may be conducted at any suitable temperature (e.g. a temperature at which the silane(s) used are in a gaseous form). For example, the gaseous phase silanization may be conducted at a temperature of from 80 to 150° C., such as about 100° C. In additional or alternative embodiments, the gaseous phase silanization process may be conducted under reduced pressure, thereby lowering the temperature at which the monomeric hydrophobic silane compound(s) become gaseous. For example, the pressure for the gaseous phase silanization process may be from 0.1 to 0.3 mbar, such as about 0.16 mbar.

The gaseous phase silanization may make use of any suitable methodology to supply the monomeric hydrophobic silane compound(s) to the activated $Ti_3C_2$ MXene layer. For example, the monomeric hydrophobic silane compound(s) may be transported in a suitable carrier gas to the activated $Ti_3C_2$ MXene layer. For example, the gaseous phase silanization may use a flow of an inert gas for this purpose. The inert gas (e.g. argon), may have any suitable flow rate, such as from 50 to 100 sccm, such as about 65 sccm.

While the method described above provides a sensor material, this material's suitability can be enhanced further by the inclusion of one or more electrodes. Thus, in embodiments of the invention, the composite material provided in step (a) of the process above may further comprise at least two electrodes laid on the surface of the activated $Ti_3C_2$ MXene layer. As will be appreciated, in embodiments where the electrodes are present, they may be laid onto the surface of the activated $Ti_3C_2$ MXene layer before that layer is coated by the hydrophobic silane layer.

The electrodes may be formed by any suitable means on the surface of the activated $Ti_3C_2$ MXene layer. For example, the electrodes may be formed by thermal evaporation of an electrode material onto the surface of the activated $Ti_3C_2$ MXene layer. The electrode material may be any suitable conductive material, such as a metal and/or a conductive form of carbon. In particular embodiments of the invention, the electrode material may be gold.

The at least two electrodes may have any suitable thickness that allows them to function as part of the sensor. For example, the at least two electrodes may each have a thickness of from 75 to 150 nm, such as about 100 nm.

As noted hereinbefore, the activated $Ti_3C_2$ MXene layer may be formed by any suitable surface activation process. In embodiments of the invention that may be mentioned herein, the activated $Ti_3C_2$ MXene layer may be formed by the steps of:

(ai) providing a composite material comprising a substrate coated by an unactivated $Ti_3C_2$ MXene layer; and (aii) activating the $Ti_3C_2$ MXene layer through a surface activation process.

The surface activation may be any suitable surface activation process. An example of a suitable surface activation process is plasma activation. In embodiments of the invention that may be mentioned herein, the surface activation process may be $O_2$ plasma activation.

As will be appreciated, the method disclosed above provided a sensor. Thus, in a further aspect of the invention, there is provided a non-polar volatile organic chemical sensor comprising:

a substrate having a substrate surface;

a $Ti_3C_2$ MXene layer coated on the substrate surface which $Ti_3C_2$ MXene layer has a $Ti_3C_2$ MXene layer surface;

at least two electrodes on the $Ti_3C_2$ MXene layer surface; and a hydrophobic silane layer on the $Ti_3C_2$ MXene layer surface, wherein the hydrophobic silane layer has a thickness of from 10 to 14 nm.

The components of the sensor are as described hereinbefore, so will not be repeated again for the sake of brevity.

As will be appreciated, the hydrophobic silane layer on the $Ti_3C_2$ MXene layer may be formed in the manner described above. Thus, in embodiments of the invention that may be mentioned herein, the hydrophobic silane layer may be formed from a monomeric hydrophobic silane compound that is selected from one or more of the group consisting of (3-aminopropyl)trimethoxysilane (APTMS), trimethoxy(octyl)silane (TEOS), trimethoxy(propyl)silane, and trimethoxymethylsilane (TEMS). For example, the monomeric hydrophobic silane compound may be trimethoxy (propyl)silane.

The non-polar volatile organic chemical sensor described herein may be capable of detecting an analyte present in an environment at a concentration of about 50 ppm (and higher). This is advantageous, as it enables the sensor to detect concentrations that are much lower than previously thought possible. As shown in the examples below, the resultant sensing responses are higher than that of pristine MXene (without silanization) even in the range of 10-40 sccm when tested with α-Pinene (a non-polar VOC).

As will be appreciated, the sensor disclosed herein may be used to detect the presence or absence of a suitable non-polar VOC, such as toluene or a terpene (e.g. α-pinene). Thus, in a further aspect of the invention, there is provided a method of detecting an analyte comprising the steps of:

(bi) exposing a non-polar volatile organic chemical sensor as described hereinbefore to an environment where the analyte is suspected to be present for a period of time; and (bii) subsequently measuring the resistance of the volatile organic chemical sensor to determine the presence or absence of the analyte in said environment.

As noted above, the analyte may be a volatile organic compound. More particularly, the volatile organic compound may be a non-polar volative organic compound. Examples of non-polar volatile organic compounds that may be mentioned herein includes, but are not limited to, α-pinene, 1-hexanol, a terpinol, phenethyl alcohol, and combinations thereof. In particular embodiments that may be mentioned herein, the volatile organic compound may be α-pinene. As mentioned above, the non-polar volatile organic chemical sensor may be capable of detecting an analyte present in the environment at a concentration of about 50 ppm (and higher).

Further aspects and embodiments of the invention will not be discussed by reference to the following non-limiting examples.

EXAMPLES

Materials

TisAlC$_2$ (≥98%) was purchased from Famouschem Technology Co., Ltd. LiF powder (powder, <100 μm, ≥99.98% trace metals basis) was purchased from Sigma-Aldrich.

Example 1. Fabrication of TMPS-Modified Ti$_3$C$_2$ MXene VOC Sensor

Preparation of Ti$_3$C$_2$ MXene Nanoflakes 1 g of TisAlC$_2$ was mixed with 20~30 mL of HCl with concentration between 9 M to 12 M for 24 h at 25° C. The mixture was then washed with deionized (DI) water by centrifugation for at least 4 times at 10000 rpm for 5 min. The sediment was collected and stored at −20° C. to reduce the dissolved oxygen. The frozen MXene sediment was then dispersed in DI water (300 mL to 500 mL) by bath sonication for 1 h with Ar gas bubbling. The MXene dispersion was subjected to centrifugation at 3000 rpm. The supernatant was then collected and stored at 4° C. for further use.

Deposition Method of Ti$_3$C$_2$ MXene Thin Film

The deposition of the Ti$_3$C$_2$ MXene was carried out by spin casting. At first, the intended substrate, glass slide, was washed by ultrasonication in acetone for 30 min. After ultrasonication, the glass slide was dried by Ar gas with an air blowing gun. The dried glass slide was then subjected to oxygen (O$_2$) plasma treatment to create the hydrophilic surface. The parameters for the oxygen plasma treatment were set following this procedure: pumping down the chamber to 9.00 E$^{-2}$ torr, applying the oxygen gas with the flow rate at 30 sccm for 1 min, and setting the RF power at 100 W and the RF frequency at 50 KHz.

After O$_2$ plasma treatment, the glass slide was directly used for spinning casting of Ti$_3$C$_2$ MXene suspension. The Ti$_3$C$_2$ MXene suspension (0.8 mg/ml to 1.5 mg/mL) was casted before the spinning the sample stage. Normally, around 400 μL of Ti$_3$C$_2$ MXene liquid was needed to fully cover the glass slide (2.5 mm×2.5 mm). The spin rate of the sample stage was programmed to have two spinning steps: first step for MXene deposition and the final step for drying of the glass slide. The spin rate of the stage was set to be 1000 rpm for 60 s and the spin rate was then ramped to 500 rpm to 2000 rpm for another 60 s for sample drying. The substrate deposited with Ti$_3$C$_2$ MXene was then dried under vacuum at room temperature (23.5° C. to 25° C.) for 24 h. After drying, the sample was taken for electrode deposition via thermal evaporation.

Fabrication of Ti$_3$C$_2$ MXene VOC Sensor

Figure 1:
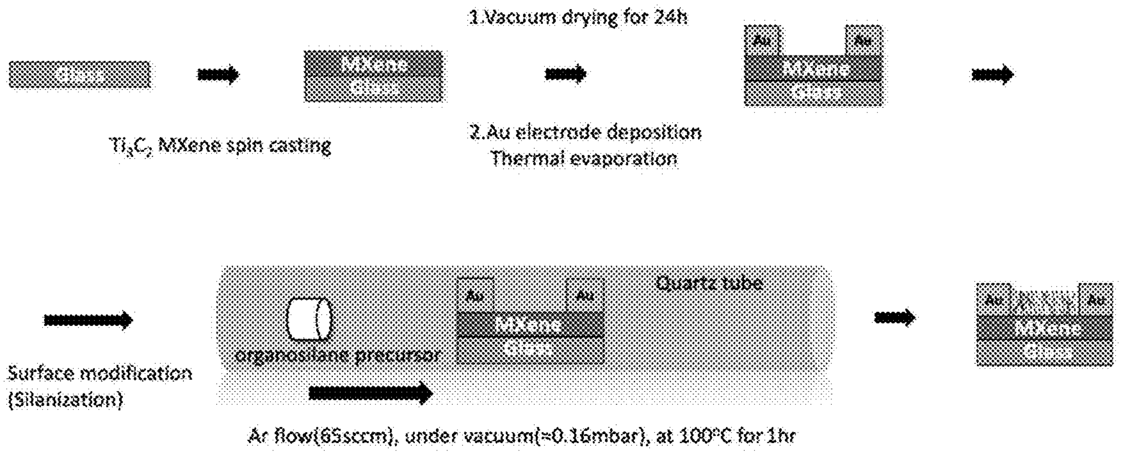
FIG. 1 depicts the schematic illustration of the fabrication procedures of $Ti_3C_2$ MXene VOC sensor.

The fabrication of Ti$_3$C$_2$ MXene VOC sensor was carried out as shown in FIG. 1. After the Ti$_3$C$_2$ thin film coated glass slide prepared above was dried for 24 h at room temperature, the sample was taken for gold (Au) electrode deposition. The deposition of the Au electrode was conducted by thermal evaporation under high vacuum at the pressure below 3×10$^{-5}$ torr. As the pressure pumped down below 3×10$^{-5}$ torr, the Au pellet fed tungsten (W) boat was heated by joule heating. The rate of Au deposition can be controlled by varying the current applied to the W boat. At first, the rate of the Au deposition was fixed at 0.1 Å/s for the first 10 nm Au layer in order to obtain better adhesion between Au and MXene layer. Later, the rate of the Au deposition was increased to 1 Å/s and the deposition was terminated when the thickness of the Au layer was 100 nm. The deposition time was about 15-20 minutes until the final thickness was 100 nm. The rate of evaporation was 1 Å/s. The as-prepared Ti$_3$C$_2$ MXene VOC sensor was immediately taken for MXene surface modification after the sample was removed from the evaporation chamber.

Surface Modification of Ti$_3$C$_2$ MXene VOC Sensor

The surface modification of the Ti$_3$C$_2$ MXene thin film on the Ti$_3$C$_2$ MXene VOC sensor prepared above was conducted by gaseous phase silanization in a tube furnace. The Au electrode-deposited Ti$_3$C$_2$ MXene-coated glass slide was placed in the middle zone of the tube furnace and 1 mL of organosilane (TMPS) was placed at the upstream side of the quartz tube around 25 cm away from the glass slide (FIG. 1). The alkyl silane replaces the hydroxyl groups of Ti$_3$C$_2$ MXene with carbon chain. During the reaction, the heating temperature was set to 100° C. with the ramping rate of temperature at 5° C./min and the flow rate of the carrier gas, Ar gas, was fixed at 65 sccm. The reaction was conducted under vacuum with the pressure of around 0.16 mbar for 1 h at 100° C. to give the TMPS-modified Ti$_3$C$_2$ MXene.

Example 2. Characterization of TMPS-Modified Ti$_3$C$_2$ MXene VOC Sensor

Figure 2:
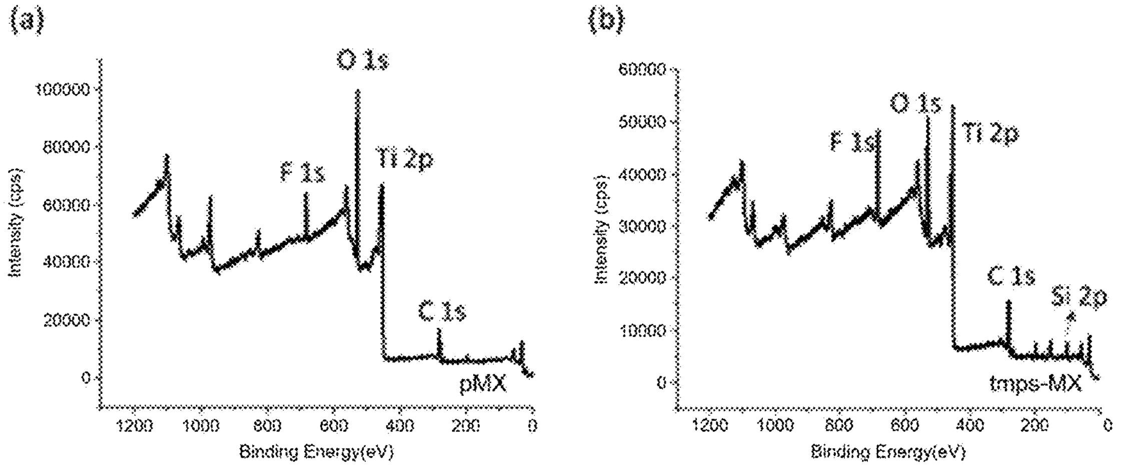
FIG. 2 depicts the X-ray photoelectron spectroscopy (XPS) wide range survey of (a) the pristine $Ti_3C_2$ MXene and (b) trimethoxy(propyl)silane (TMPS)-modified $Ti_3C_2$ MXene.
Figure 3:
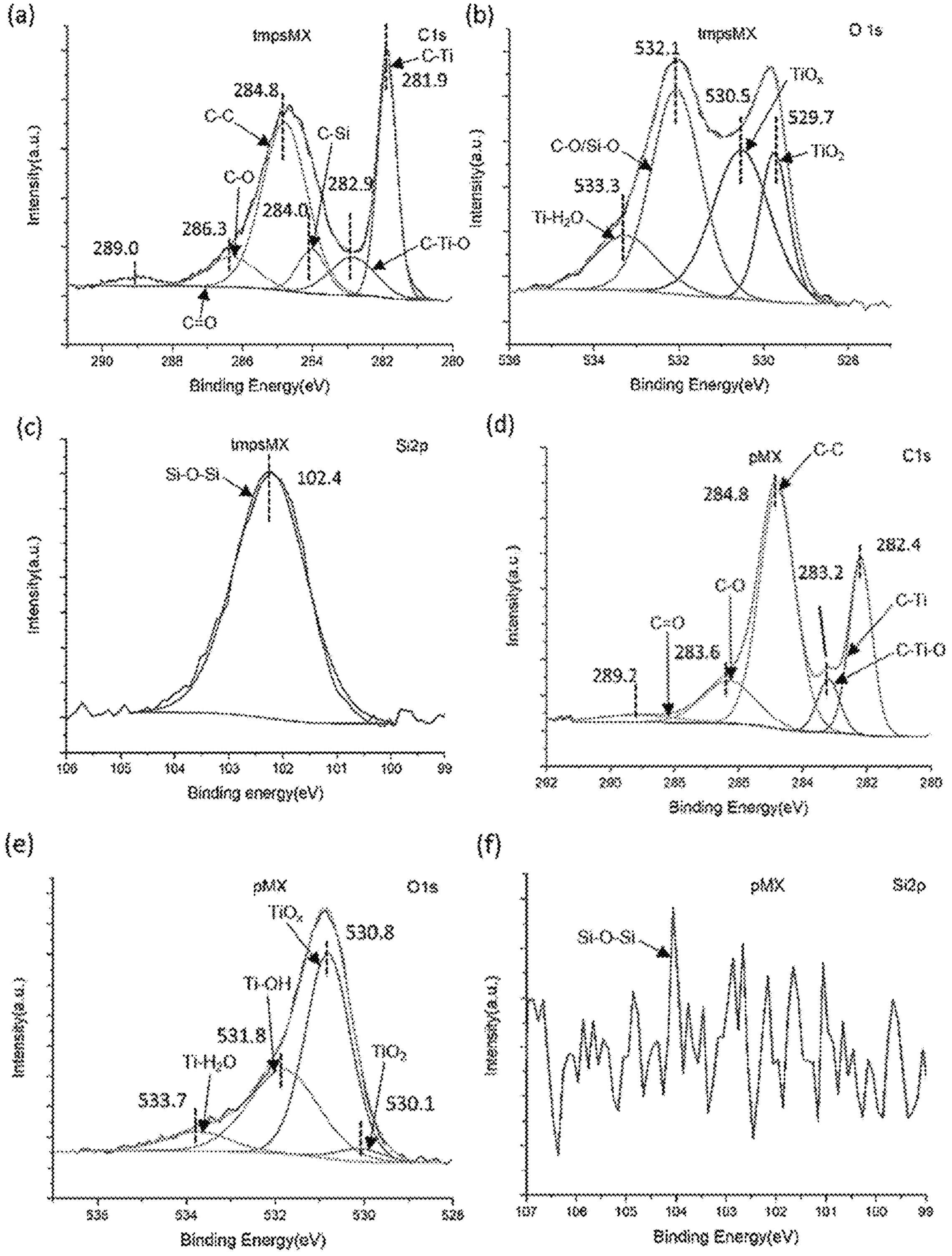
FIG. 3 depicts the XPS spectrum of TMPS-modified $Ti_3C_2$ MXene (tmpsMX) after gaseous phase silanization with measured core level of (a) C1 s, (b) O1 s and (c) Si2p and the measured core level of pristine $Ti_3C_2$ MXene (pMX) at (d) C1 s, (e) O1 s and (f) Si2p.

The evidence that the TMPS was modified on the surface of Ti$_3$C$_2$ MXene was verified by XPS as shown in FIG. 2. The Si 2*p* peak is found at around 100 eV in TMPS-modified Ti$_3$C$_2$ MXene (FIG. 2), indicating the chemical binding between TMPS and Ti$_3$C$_2$ MXene. To further investigate the chemical composition and the binding information after Ti$_3$C$_2$ MXene was modified with TMPS, narrow range scanning of XPS was performed. The TMPS-modified Ti$_3$C$_2$ MXene presents six deconvoluted peaks at, 281.9 eV, 282.9 eV, 284.0 eV, 284.8 eV, 286.3 eV and 289.0 eV, which can be assigned to the binding of Ti—C, C—Ti—O, C—Si, C—C, C—O, and C═O respectively (FIG. 3(*a*)). As compared to the spectrum of TMPS-modified Ti$_3$C$_2$ MXene (FIG. 3(*a*)), the pristine Ti$_3$C$_2$ MXene shows less deconvoluted peaks with the binding energy centered at 282.4 eV, 283.2 eV, 284.8 eV, 283.6 eV and 289.2 eV, which can be assigned to the binding of C—Ti, C—Ti—O, C—C, C—O, and C═O (FIG. 3(*d*)). Since the pristine Ti$_3$C$_2$ MXene was treated with Ar plasma to remove the surface oxide and contamination, some of the termination group on the C—Ti bonding was also removed, leading to higher measured Ti—C binding energy at 282.4 eV as compared to the TMPS-modified Ti$_3$C$_2$ MXene at 281.9 eV (J. Halim et al., *Appl. Surf. Sci.* 2016, 362, 406-417; S. Shah et al., *Chem. Commun.* 2017, 53, 400-403; and W. Y. Chen et al., *ACS Nano* 2020, 14, 11490-11501). Also, the formation of C—Si binding is found at 282.9 eV after surface silanization with TMPS, which suggests that the TMPS molecules are covalently bond to the MXene surface.

Example 3. Resistance of Pristine Ti$_3$C$_2$ MXene and TMPS-Modified Ti$_3$C$_2$ MXene The resistance of the Ti$_3$C$_2$ MXene thin film and TMPS-modified Ti$_3$C$_2$ MXene was measured by the two-terminal method.

Two-Terminal Method

To test the conductivity of the sensor, the sensor was subjected to two terminal I-V test under pure N$_2$ exposure.

The purging conditions were until the resistance stabilized and there was no or very little change in resistance observed when it was exposed to nitrogen. Nitrogen was purged at 200 sccm flow rate during this time. The sensor typically has a linear I-V characteristic for an applied voltage between −1V to 1V.

Results and Discussion

Figure 4:
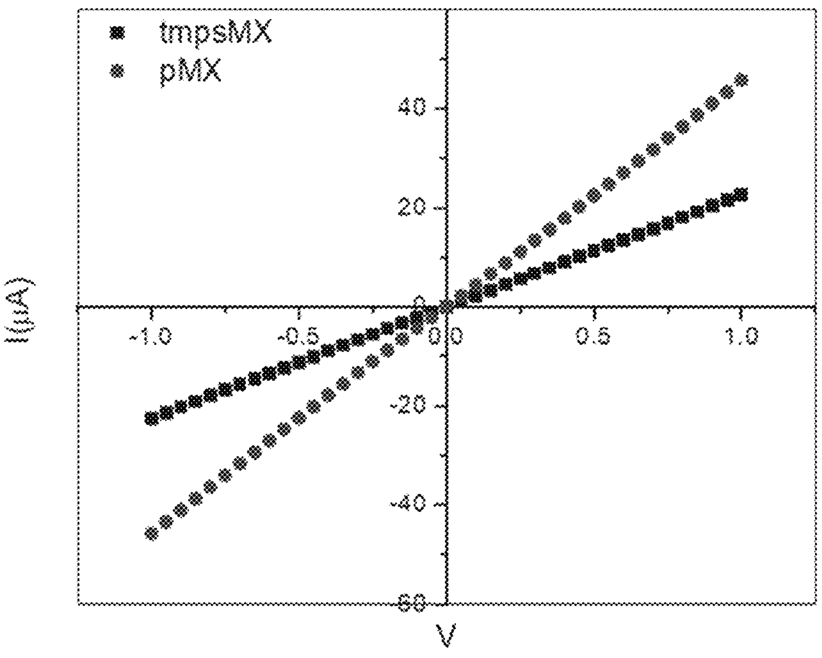
FIG. 4 depicts the I-V curve measured from pristine $Ti_3C_2$ MXene (pMX) VOC sensor, and TMPS-modified $Ti_3C_2$ MXene (tmps-MX) VOC sensor via two-terminal method.

The linear I-V curve shows the ohmic behavior and indicates the stable conductance of the pristine and TMPS-modified $Ti_3C_2$ MXene thin film (FIG. 4). The resistance of the pristine and TMPS-modified $Ti_3C_2$ MXene was then calculated by ohm's law, showing the resistance of pristine $Ti_3C_2$ MXene at 22.03 kΩ and TMPS-modified $Ti_3C_2$ MXene at 44.35 kΩ.

Example 4. VOC Sensing Performance of Pristine $Ti_3C_2$ MXene and TMPS-Modified $Ti_3C_2$ MXene The existence of the carbon chain can improve the affinity of the non-polar VOCs towards $Ti_3C_2$ MXene, thereby increasing the sensing response of the non-polar VOCs.

VOC Sensing Performance Test

To measure the gas sensing response of the sensor (pristine $Ti_3C_2$ MXene or TMPS-modified $Ti_3C_2$ MXene), the sensor was placed in a gas sensing chamber with an inlet and an outlet of gas channel. In addition, a simple probe station was installed with the gas sensing system to obtain the electrical signal from the MXene sensors.

The generation of the VOC vapors was carried out by the bubbling of carrier gas ($N_2$) through the pure VOC chemicals. The concentration of the VOC can be controlled by the flow rate of $N_2$ blowing through the bubbler and the dilution gas ($N_2$) during gas mixing. The total flow rate of the $N_2$ was fixed at 200 sccm during the measurement. The concentration of the VOC was calculated following the equation (1):

$$\text{Concentration } (ppm) = \left(\frac{P_s}{P} \times \frac{f}{f+F}\right) \times 10^6 \quad (1)$$

Where $P_s$ refers to the saturated partial pressure in mm-Hg and P refers to the total pressure; f and F refer to the flow rate of the VOC line and the dilution line, respectively. The saturated partial pressure of VOC can be calculated from Antoine equation (2):

$$\text{Log}P_s = \left(A - \frac{B}{C+T}\right) \quad (2)$$

Where A, B and C are the Antoine coefficients and T is the temperature in Kelvin.

To investigate the VOC sensing performance, TMPS-modified $Ti_3C_2$ MXene and pristine $Ti_3C_2$ MXene were exposed to α-Pinene (a terpene and non-polar plant VOC) with various concentration from 50 ppm to 2500 ppm (50 ppm, 100 ppm, 1000 ppm or 2500 ppm). The sensing of α-Pinene can be observed by the change in the resistance as the pristine and TMPS-modified $Ti_3C_2$ MXene were applied with a constant DC voltage. The sensing response was calculated following the equation (3):

$$\text{Gas sensing response } (\%) = \Delta R/R_0 \times 100 = (R_g - R_0)/R_0 \times 100 \quad (3)$$

Where $R_0$ and $R_g$ refer to the resistance of the sensor in the $N_2$ and exposed to the analytes.

Results and Discussion

From FIG. 5 and Table 1, the TMPS-modified $Ti_3C_2$ MXene showed improved sensing response towards α-Pinene at 0.06%, 0.04%, 0.93%, 2.36%, 4.78% for 50 ppm, 100 ppm, 1000 ppm, and 2500 ppm, respectively, as compared to pristine $Ti_3C_2$ MXene. For instance, the sensing response of α-Pinene in TMPS-modified $Ti_3C_2$ MXene was 2.36% at 1000 ppm, whereas the sensing response detected by pristine $Ti_3C_2$ MXene was 0.74%. Additionally, the TMPS-modified $Ti_3C_2$ MXene showed a signal even at the lower limit of the detection range at 50 ppm and below, while the pristine $Ti_3C_2$ MXene did not show obvious signal under such low concentration of α-Pinene, which exhibits the improved sensing specificity of non-polar VOC by $Ti_3C_2$ MXene-based VOC sensor.

TABLE 1

The summarized gas sensing response of α-Pinene by pristine and TMPS-modified $Ti_3C_2$ MXene.

| Concentration | 2500 ppm | 1000 ppm | 500 ppm | 100 ppm | 50 ppm |
|---|---|---|---|---|---|
| pMX | 1.33% | 0.74% | 0.5% | N/A | N/A |
| tmpsMX | 4.78% | 2.36% | 0.93% | 0.04% | 0.06% |

N/A: data not available due to unidentifiable signal to noise ratio.

The invention claimed is:

1. A method of manufacturing a non-polar volatile organic chemical sensor, the method comprising the steps of:
(a) providing a composite material comprising a substrate coated by an activated Ti3C2 MXene layer, wherein the activated Ti3C2 MXene layer has a surface; and
(b) forming a hydrophobic silane layer on the surface of the activated Ti3C2 MXene layer to provide the non-polar volatile organic chemical sensor, wherein the hydrophobic silane layer is formed by gaseous phase silanization using a monomeric hydrophobic silane compound.

2. The method according to claim 1, wherein the monomeric hydrophobic silane compound is selected from one or more of the group consisting of (3-aminopropyl)trimethoxysilane (APTMS), trimethoxy(octyl)silane (TEOS), trimethoxy(propyl)silane, and trimethoxymethylsilane (TEMS).

3. The method according to claim 2, wherein the monomeric hydrophobic silane compound is trimethoxy(propyl) silane.

4. The method according to claim 1, wherein the hydrophobic silane layer has a thickness of from 10 to 14 nm.

5. The method according to claim 1, wherein the gaseous phase silanization is conducted at from 80 to 150° C. and a pressure of from 0.1 to 0.3 mbar.

6. The method according to claim 1, wherein the gaseous phase silanization used a flow of an inert gas at a flow rate of from 50 to 100 sccm.

7. The method according to claim 1, wherein the composite material provided in step (a) of claim 1 further comprises at least two electrodes laid on the surface of the activated $Ti_3C_2$ MXene layer.

8. The method according to claim 7, wherein the electrodes are formed by thermal evaporation of an electrode material onto the surface of the activated $Ti_3C_2$ MXene layer.

9. The method according to claim 1, wherein the activated $Ti_3C_2$ MXene layer is formed by the steps of:

(ai) providing a composite material comprising a substrate coated by an unactivated $Ti_3C_2$ MXene layer; and (aii) activating the $Ti_3C_2$ MXene layer through a surface activation process.

10. The method according to claim 9, wherein the surface activation process is plasma activation.

11. A non-polar volatile organic chemical sensor comprising:

a substrate having a substrate surface;

a Ti3C2 MXene layer coated on the substrate surface wherein the Ti3C2 MXene layer has a Ti3C2 MXene layer surface;

at least two electrodes on the Ti3C2 MXene layer surface; and a hydrophobic silane layer on the Ti3C2 MXene layer surface, wherein the hydrophobic silane layer has a thickness of from 10 to 14 nm.

12. The sensor according to claim 11, wherein the hydrophobic silane layer is formed from a monomeric hydrophobic silane compound that is selected from one or more of the group consisting of (3-aminopropyl)trimethoxysilane (APTMS), trimethoxy(octyl)silane (TEOS), trimethoxy(propyl)silane, and trimethoxymethylsilane (TEMS).

13. The sensor according to claim 12, wherein the monomeric hydrophobic silane compound is trimethoxy(propyl)silane (TMPS).

14. The sensor according to claim 11, wherein:

(I) the electrode material is gold;

(II) the at least two electrodes each have a thickness of from 75 to 150 nm;

(III) or both (I) and (II).

15. The sensor according to claim 11, wherein the non-polar volatile organic chemical sensor is capable of detecting an analyte present in an environment in a concentration of about 50 ppm.

16. A method of detecting an analyte comprising the steps of:

(bi) exposing a non-polar volatile organic chemical sensor as described in claim 11 to an environment where the analyte is suspected to be present for a period of time; and (bii) subsequently measuring the resistance of the volatile organic chemical sensor to determine the presence or absence of the analyte in said environment.

17. The method according to claim 16, wherein the analyte is a volatile organic compound.

18. The method according to claim 17, wherein the volatile organic compound is selected from one or more of α-pinene, 1-hexanol, a terpinol, and phenethyl alcohol.

19. The method according to claim 16 wherein the non-polar volatile organic chemical sensor is capable of detecting an analyte present in the environment in a concentration of about 50 ppm.

* * * * *